United States Patent
Evreinov et al.

(10) Patent No.: US 9,672,701 B2
(45) Date of Patent: Jun. 6, 2017

(54) TACTILE IMAGING SYSTEM

(71) Applicants: TAMPEREEN YLIOPISTO, Tampereen yliopisto (FI); FUKOKU CO., LTD., Ageo-shi, Saitama (JP)

(72) Inventors: Grigori Evreinov, Tampere (FI); Ahmed Farooq, Tampere (FI); Roope Raisamo, Tampere (FI); Arto Hippula, Tampere (FI); Daisuke Takahata, Saitama (JP)

(73) Assignees: TAMPEREEN YLIOPISTO, Tampereen Yliopisto (FI); FUKOKU CO., LTD., Saitama (JP)

( * ) Notice: Subject to any disclaimer, the term of this patent is extended or adjusted under 35 U.S.C. 154(b) by 0 days.

(21) Appl. No.: 14/794,264

(22) Filed: Jul. 8, 2015

(65) Prior Publication Data

US 2016/0012689 A1 Jan. 14, 2016

(30) Foreign Application Priority Data

Jul. 9, 2014 (JP) .................. 2014-141263

(51) Int. Cl.
| | | |
|---|---|---|
| H04B 3/36 | (2006.01) | |
| G08B 6/00 | (2006.01) | |
| A61B 5/053 | (2006.01) | |
| A61N 1/36 | (2006.01) | |
| G06F 3/01 | (2006.01) | |

(52) U.S. Cl.
CPC .............. *G08B 6/00* (2013.01); *A61B 5/0531* (2013.01); *A61N 1/36* (2013.01); *G06F 3/016* (2013.01)

(58) Field of Classification Search
None
See application file for complete search history.

(56) References Cited

U.S. PATENT DOCUMENTS

| | | | |
|---|---|---|---|
| 4,542,375 A | 9/1985 | Alles et al. | |
| 4,816,811 A | 3/1989 | Bogatin et al. | |
| 5,631,861 A | 5/1997 | Kramer | |
| 5,782,873 A | 7/1998 | Collins | |
| 6,032,074 A | 2/2000 | Collins | |
| 6,726,638 B2 * | 4/2004 | Ombrellaro ............ | A61B 5/103 600/587 |
| 7,077,015 B2 | 7/2006 | Hayward et al. | |
| 7,375,454 B2 | 5/2008 | Takasaki | |
| 7,740,953 B2 | 6/2010 | Jackson et al. | |

(Continued)

OTHER PUBLICATIONS

De Rossi et al., "Electroactive polymer patches for wearable haptic interfaces", 33rd Annual International Conference of the IEEE EMBS, Aug. 30-Sep. 3, 2011, 4 pages.

(Continued)

*Primary Examiner* — Adolf Dsouza
(74) *Attorney, Agent, or Firm* — Andrew M. Calderon; Roberts Mlotkowski Safran Cole & Calderon, P.C.

(57) ABSTRACT

One embodiment of the present invention provides a tactile imaging system. The tactical imaging system includes: a receptive field tactile control unit; and a connecting module configured to connect the tactile imaging system with a host system. In addition, the receptive field tactile control unit includes: a monitoring module configured to monitor a property of a human skin; and a tactile stimulation providing module configured to provide a tactile stimulation.

18 Claims, 4 Drawing Sheets

(56) References Cited

U.S. PATENT DOCUMENTS

| | | | |
|---|---|---|---|
| 7,887,729 B2 | 2/2011 | Tye et al. | |
| 8,033,189 B2 | 10/2011 | Hayakawa et al. | |
| 8,040,223 B2 | 10/2011 | Mortimer et al. | |
| 8,253,703 B2 | 8/2012 | Eldering | |
| 8,362,882 B2 | 1/2013 | Heubel et al. | |
| 8,378,797 B2 | 2/2013 | Pance et al. | |
| 8,568,642 B2 | 10/2013 | Jackson et al. | |
| 2011/0301441 A1* | 12/2011 | Bandic | A61B 5/0059 600/306 |
| 2012/0328349 A1 | 12/2012 | Isaac et al. | |

OTHER PUBLICATIONS

Park et al., "Soft Artificial Skin with Multi-Modal Sensing Capability Using Embedded Liquid Conductors", IEEE, 2011, 4 pages.
Gennisson et al., "Assessment of Elastic Parameters of Human Skin Using Dynamic Elastography", IEEE, vol. 51, No. 8, Aug. 2004, 10 pages.
Kim et al., "A transparent and stretchable graphene-based actuator for tactile display", IOP Publishing, Nanotechnology 24, 2013, 8 pages.
Arai et al., "Transparent Tactile Feeling Device for Touch-Screen Interface", Proceedings of the 2004 IEEE International Workshop, Sep. 2004, 6 pages.
Mortimer et al., "Vibrotactile transduction and transducers", Engineering Acoustics, Acoustical Society of America, 2007, 8 pages.
Carpi et al., "Electroactive Polymer-Based Devices for e-Textiles in Biomedicine", IEEE, vol. 9, No. 3, Sep. 2005, 24 pages.

* cited by examiner $S_{t1}$ – test signal (subthreshold haptic signal) generated from actuator 114

$S_{t2}$ – test signal (subthreshold non-contact signal) generated from emitter 113

$S_h$ – haptic information signal generated from actuator 114

$S_s$ – impact signal generated upon direct-contact or
short-distance-confrontation between human skin 102 and mediator 112

TACTILE IMAGING SYSTEM

CROSS-REFERENCE TO RELATED APPLICATION(S)

This application claims priority from JP Patent Application No. 2014-141263 filed on Jul. 9, 2014, the entire contents of which are incorporated herein by reference.

TECHNICAL FIELD

The present invention relates generally to tactile imaging systems and in particular to a device and a method for enhancing the response of human skin to tactile stimuli.

BACKGROUND ART

The stimulation of the human is the process by which the energy from a source in a kind of periodic alterations of the energy flow impacts on the human body, usually the skin or a body segment. Alterations and redistribution of mechanical, thermal, electrical or electromagnetic energy (called stimulus) are transformed by sensory receptors of the skin into feelings interpreted as tactile information (periodic heat, skin displacements/stretch, sense of pressure/force, pushes or pulses and vibrations, squeeze, tickling, tingling). Feelings associated with physical processes can take place or be generated in the field of contact, beneath or above the surface.

The need for the use of tactile information channel and simulation of the tactile feelings led to development of tactile actuators (thermal/infra-red, pneumatic, ultrasonic, electromagnetic, hydraulic, electrical and mechanical). However, since there are intermediate components between the source (actuator) and the specific receptors in the skin, a signal traveling from the source to the specific receptors may be lowered in terms of magnitude, and may be changed in terms of phase due to impedance of each intermediate component. Such distorted signal may be easily affected by external noise. These factors affect on transmission/propagation of tactile stimuli through different materials and substances having different structure and physical properties that can alter/dissipate energy of stimuli by making tactile signals weak and less informative as expected.

To account for noise and other disturbances, it was adopted that the energy alteration of applied tactile stimuli should exceed 24 dB above the sensitivity threshold for hairy skin (e.g., Mortimer B. J. P. et al. "*Vibrotactile transduction and transducers*" J. Acoust. Soc. Am., 2007, 121(5), 2970-2977).

Some efforts have already been undertaken to change the conditions for propagation of mechanical energy of tactile stimuli to skin receptors (e.g., De Rossi D., et al. "Electroactive polymer patches for wearable haptic interfaces" Conf. Proc. IEEE Eng. Med. Biol. Soc., 2011, 8369-8372, Carpi F. et al. "*Electroactive Polymer-Based Devices for e-Textiles in Biomedicine*" IEEE Trans. on Information Tech. in Biomedicine, 2005, 9(3), 295-318, Kim U. et al. "*A transparent and stretchable graphene-based actuator for tactile display*" Nanotechnology, 2013, 24, 145501, U.S. Pat. No. 7,375,454-B, U.S. Pat. No. 8,362,882-B) by placing actuators in a direct contact with human skin (smart fabrics/e-textiles and coverings), through compensation/suppression of disturbances, external noise and surround vibrations by making an exact (easy distinguishable) waveform of stimuli in a specific location due to detection of tactile stimuli propagation to a destination field of contact (e.g., U.S. Pat. No. 8,378,797-B), or by observing the result of skin deformation (variations in skin strain) in the field of contact and adapting the applied magnitude of tactile stimuli (e.g. U.S. Pat. No. 7,077,015-B). However, when the skin deformation occurs, that is, when e.g., fingers grip a rigid surface or fingertips act against a rigid surface or froze, protected with gloves, the skin receptors may be blocked even for higher level energy alterations which significantly exceed 24 dB above the skin sensitivity threshold, thereby making the proposed solutions inefficient.

Another way of improving the response of the human skin consists in altering sensitivity of skin receptors. Inventions, which relate to improving the sensory parameters of touch, in particular, to lower the threshold of skin receptors, have been disclosed in U.S. Pat. No. 5,782,873-A and U.S. Pat. No. 6,032,074-A. The method includes locating a receptive area where the function of receptors should be enhanced and applying a bias signal to this (skin) area before the informative (tactile) signals will be presented, perceived and identified. At that, the bias signals might have the same or different nature such as non-specific electrical or mechanical (gas/air flow) stimulation, than informative tactile signals. Such an approach can be efficient with optimal parameters of bias signals which have to be calibrated in advance. Nevertheless, parameters of the skin vary significantly and affected by many different factors of physical, physiological (humoral), and psychological nature. Therefore, it is difficult to predict whether a sensitivity change will happen or not within the predefined time interval and such a technique cannot easily be realized in practice. U.S. Pat. No. 8,040,223-B also discloses a method that includes the steps of temporarily altering the threshold of vibrational detection prior to the onset of tactile stimulus to achieve improved detection of the vibrotactile alert or communication signals without increasing the vibratory displacement amplitude. However, such an approach does not eliminate the problems of signal propagation to tactile receptors for sub-sensory vibrational stimuli that has to change sensitivity of the skin within the predefined time interval. Skin sensitivity depends on different factors of physical, physiological (humoral), and psychological nature. This approach is also constrained by specific parameters of vibration and conditions of tactile stimulation.

U.S. Pat. No. 8,253,703-B discloses a tactile interface that includes a plurality of individually controllable piezoelectric drivers positioned around a perimeter of a highly tensioned elastomeric material such as silicone rubber, polybutadiene, nitrile rubber, as well as other rubbers and elastomers. Driver circuitry can apply control information to each of the plurality of individually controllable drivers to produce a wave pattern in the tensioned elastomeric material. However, interaction through elastomeric material covering a stiff surface and having a density higher than human skin will squeeze the skin and increase the perceptual threshold by damping the response of skin receptors to tactile stimuli. Depending on a loss modulus, elastomeric materials may absorb the exerted energy to thereby alter the value and sense of the applied stimuli.

Another technical solutions are overlays and coverings, which allow to adjust a density of the surface of interaction. In particular, deformable overlays have been initially designed to detect the pressure and position of the fingertip on CRT displays, as disclosed in U.S. Pat. No. 4,542,375-A and U.S. Pat. No. 4,816,811-A, then to improve different strength and force envelops on the fingertip when pressing virtual keys of on-screen keyboards (e.g., US-2012-328349-A and Arai F. et al. "*Transparent tactile feeling*

*device for touch-screen interface*" Proc. of the 2004 IEEE Int. Workshop on Robot and Human Interactive Communication, 2004, 527-532). The overlays and coverings can be filled in with a liquid or gel-like substance having a density similar to the density of hypodermis of the human skin, which is typically about of 1100 kg/m3 (e.g. Gennisson, J.-L. et al. "*Assessment of Elastic Parameters of Human Skin Using Dynamic Elastography*" IEEE Trans. on Ultrasonics, Ferroelectrics, and Freq. Control, 2004, 51(8), 980-989). However, these solutions have fixed/static parameters and do not allow changing them to control the result and efficiency of tactile stimulation.

In recent years, the advancements in robotics also enhanced the research and development of the soft artificial skins with multi-modal sensing capability (e.g., Park Y. et al. "*Soft Artificial Skin with Multi-Modal Sensing Capability Using Embedded Liquid Conductors*" IEEE Sensors, 2012, 12(8), 2711-2718, U.S. Pat. No. 8,033,189-B, U.S. Pat. No. 7,887,729-B, U.S. Pat. No. 7,740,953-B), and even having embedded elastomeric actuation points to simulate skin movements of facial expression (e.g., U.S. Pat. No. 8,568,642-B). However, a functionality of artificial skins is limited to sensing the contact event and actuation for imaging the specific patterns (e.g., facial traits) that can be visually recognized by human in the context of interaction scenario. That is, artificial robotic skins still are not intended to support processing and conditions of human touch and cannot be used as efficient tactile imaging system to mediate tactile-based interaction of the human in different environments (aggressive, dangerous or in artificial reality).

SUMMARY OF INVENTION

An aspect of the present invention provides a tactile imaging system including: a receptive field tactile control unit; and a connecting module configured to connect the tactile imaging system with a host system, wherein the receptive field tactile control unit includes: a monitoring module configured to monitor a property of a human skin; and a tactile stimulation providing module configured to provide a tactile stimulation.

According to the above-mentioned configuration, it is possible to provide the tactile imaging system which can appropriately suppress/compensate the external noise.

DETAILED DESCRIPTION OF EMBODIMENT

Figure 1:
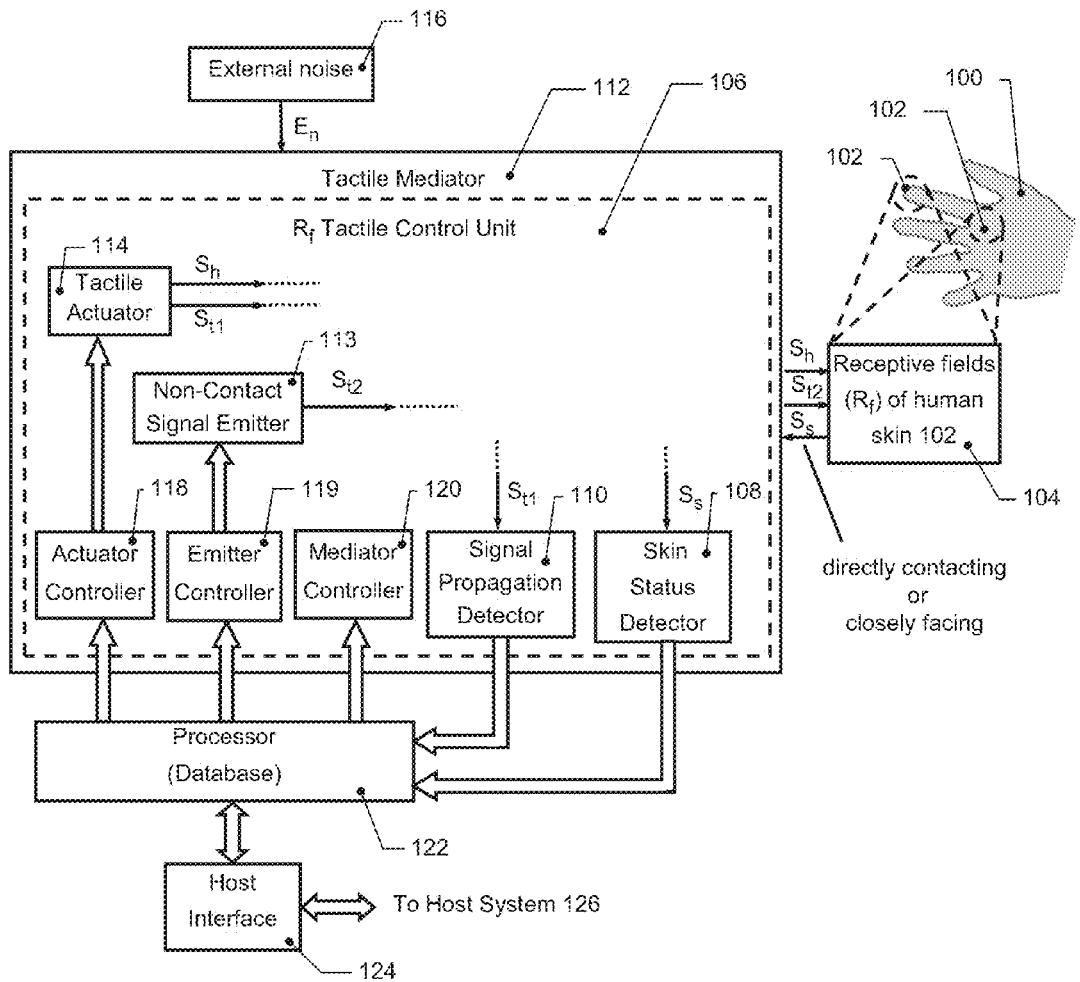
FIG. 1 illustrates a tactile imaging system according to an embodiment

The embodiments will be described with reference to the accompanying drawings. In the drawings and the description, the same reference numbers are used to refer to the same or like parts.

The system according to the embodiment is able to dynamically adapt parameters of tactile stimuli to avoid the problems exhibited when the skin sensitivity threshold has been changed due to any reason, e.g., when human fingers grip a rigid surface, or fingertips were squeezed when acting against a rigid surface, or fingers froze or/and have been protected by gloves and due to other reason.

The tactile imaging system includes a receptive field tactile control unit and a processor. The system collects information about skin contact status and conditions for propagation of tactile signals (stimuli), and generates the tactile stimuli having parameters appropriate for efficient transfer and imaging tactile information according to the host's needs (preferences, scenario/behavior or the context of use) based on the collected information.

The tactile imaging system further includes a host interface through which the tactile imaging system is connected with the host system. The receptive field tactile control unit includes an actuator, a deformable mediator, a monitoring module configured to monitor both skin status and propagation of tactile signals from actuator to the receptive field of the skin, a compensation module configured to compensate external noise, and electronic components configured to control functionality of the actuator, properties of the mediator, and the skin contact status.

An example of FIG. 1 includes an Rf tactile control unit 106, a processor 122 and a host interface 124. The Rf tactile control unit 106 includes a tactile actuator 114, an actuator controller 118, a non-contact signal emitter 113, an emitter controller 119, a tactile mediator 112, a mediator controller 120, a skin status detector 108 and a signal propagation detector 110. In reality, the tactile mediator 112 may embed all the other components thereinto, and thus, the Rf tactile control unit 106 may be realized in the tactile mediator 112, as shown in FIG. 1.

The tactile mediator 112 is to be brought into contact with the human skin 102 (the receptive field 104 thereof), and generates a skin contact impact signal Ss upon contact with the human skin 102. The state of "contacting" includes not only the status of directly contacting, but also the status of closely facing via a short-distance gap. The skin status detector 108 detects the impact signal Ss. The mediator controller 120 controls a parameter of the tactile mediator 112.

In this embodiment, the tactile mediator 112 is an active composite substance including embedded active components such as electroactive polymeric fibers or fabrics which can emit heat and humidity, IR-emission and radio frequency (RF) for measuring the electrical impedance, or generate acoustic waves for measuring mechanical impedance. The embedded active component functions as the non-contact signal emitter 113. The non-contact signal emitter 113 is capable of emitting a test signal St2 which is a subthreshold non-contact signal. The emitter controller 119 controls the non-contact signal emitter 113.

The tactile actuator 114 is capable of generating a haptic information signal Sh and a test signal St1 which is a subthreshold haptic signal. The haptic information signal Sh is, for example, a human-perceivable vibration having the specific envelope (specific attack, sustain and decay) from 80 to 500 ms. The haptic information signal Sh may be composed of different group of pulses. For example, the haptic information signal Sh may be composed of five pulses with about 100 Hz and eight pulses with about 10 Hz. On the other hand, the test signal St1 is, for example, a human-imperceivable vibration. The test signal St1 may be very short (e.g., from 10 to 50 ms) in terms of duration, and/or very weak in terms of magnitude. The actuator controller 118 controls the tactile actuator 114.

The signal propagation detector 110 detects the test signal St1 through the tactile mediator 112. The signal propagation detector 110 is particularly positioned so that, while the test signal St1 is propagated thereto, the contact signal Ss is not propagated thereto.

When the tactile imaging system receives an initialization signal from a host system 126, a processor 122 determines whether the tactile mediator 112 is in contact (directly contacting or closely facing) with the skin or not, for example, based on a detection result of the skin status detector 108. When no contact with the tactile mediator 112 has been detected and the tactile actuator 114 is not required to generate the haptic information signal Sh, a processor 122 starts a background information assessment.

In the background information assessment, the tactile actuator 114 generates a test signal St1, and the signal propagation detector 110 detects the test signal St1 affected by an external noise 116 applied to the tactile mediator 112. The external noise 116 may include, for example, an inherent mechanical vibration of the tactile actuator 114. Then, the measured external noise 116 is compared with a reference value which is previously stored in a database in the processor 122 or in the host system 126. If the difference is less than a threshold (e.g., less than 30%), this value will be updated; otherwise the system will further refer to the value taken from the database.

Similarly, pressure/force, temperature, humidity and infra-red (IR) energy radiation may be collected through the skin status detector 108. Alternatively/additionally, information, such as a skin impedance, a template of the IR-PPG (photoplethysmographic) signal, may be read from the database.

After the background information assessment is completed, the system starts to continuously track a detection result of the signal propagation detector 110 which indicates a propagation of the test signal St1 from the tactile actuator 114, and the detection result of the skin status detector 108 which indicates a propagation of a test signal St2 from the tactile mediator 112 through the receptive field 104 of the skin 102 contact to thereby evaluate the skin properties (e.g., electrical impedance, pressure/force, temperature, humidity and an image distribution of the infra-red (IR) energy radiation and skin strain). The test signal St1 is generated by the tactile actuator 114 using the actuator controller 118, and the test signal St2 is radiated/emitted from the non-contact signal emitter 113 using the emitter controller 119.

The signal to be received by the signal propagation detector 110 will contain both the test signal St1 generated from the tactile actuator 114 and the component En of the external noise 116. On the other hand, the signal to be received by the skin status detector 108 will contain both the component En of the external noise 116 and the skin contact impact signal Ss which is applied onto the surface of the tactile mediator 112 upon contact between the tactile mediator 112 and the human skin 102. The processor 122 extracts an attenuation constant and a phase constant from the test signal St1 and the test signal St2, and performs a control to optimize the parameters (mechanical, electrical, thermal) of the tactile mediator 112 so as to decrease or compensate the external noise 116 by optimizing a propagation condition for the tactile/haptic information Sh which is a perceivable signal or pattern applied to the receptive field 104 of the human skin 102. The tactile/haptic information Sh may be applied to the receptive field 104 of the human skin 102 through the direct contact between the tactile mediator 112 the human skin 102, through a small distance gap, or through an object such as the glove.

In summary, the detection result of the signal propagation detector 110 and the detection result of the skin status detector 108 in this embodiment are as follows.

TABLE 1

| condition | Detection Result of Signal Propagation Detector 110 | Detection Result of Skin Status Detector 108 |
| --- | --- | --- |
| St1 ≠ 0 | $k_M * (St1 + En)$ | $k_C * (St1 + En + Ss)$ |
| St1 = 0 | $k_M * (En)$ | $k_C * (En + Ss)$ |

$k_M$ is a factor depending on the tactile mediator 112. $k_M$ ranges from 0 to N (N is a number equal to or larger than 1). $k_C$ is a factor depending on the skin contact status between the tactile mediator 112 and the receptive field 104 of the skin 102. $k_C$ ranges from 0 to 1. The condition $k_C=1$ corresponds to the situation that the tactile mediator 112 contacts the entire area of the receptive field 104 of the skin 102.

In this embodiment, templates/samples of the test signal St1 and the skin contact impact signal Ss are stored in the database. More specifically, as the template/sample of the test signal St1, the detection result of the signal propagation detector 110 when $k_M=1$ and En=0 is stored. Further, as the template/sample of the skin contact impact signal Ss, the detection result of the skin status detector 108 when $k_C=1$ (full contact), St1=0 and En=0 is stored.

In particular, the processor 122 controls the actuator controller 118, the emitter controller 119 and the mediator controller 120 to perform the above-mentioned adjustment. Various methods can be applied to change the parameters of tactile mediator 112. For example, the tactile mediator 112 may have the polymer structure which is sensitive to the light having a specific spectrum, so that density or elasticity of the tactile mediator 112 can be modulated by being irradiated with a mesh of embedded LEDs. Alternatively, noise signal propagation may be diminished in a specific direction, or a disturbance in a given frequency range may be fully compensated.

Alternatively, an embedded mesh of elastomeric micro-/nano-actuators or fabrics may be controlled electrically. Nano-pipes filled in with a magneto-rheological substance may be controlled by magnetic field. Or whatever technology suitable for any skilled in the art may be used. For example, a composite gel-like substance, such as electrorheological fluid, which is safety and possible to be applied in the tactile mediator 112 which has to be in contact with human skin 102 may be used.

Other parameters, which are related to the contact with human skin 102, such as heating/cooling conditions, humidity and electrical impedance may be measured and adjusted accordingly. For instance, the temperature/humidity conditions may be adjusted by using air flow circulating through the porous surface of the contact area.

Figure 2:
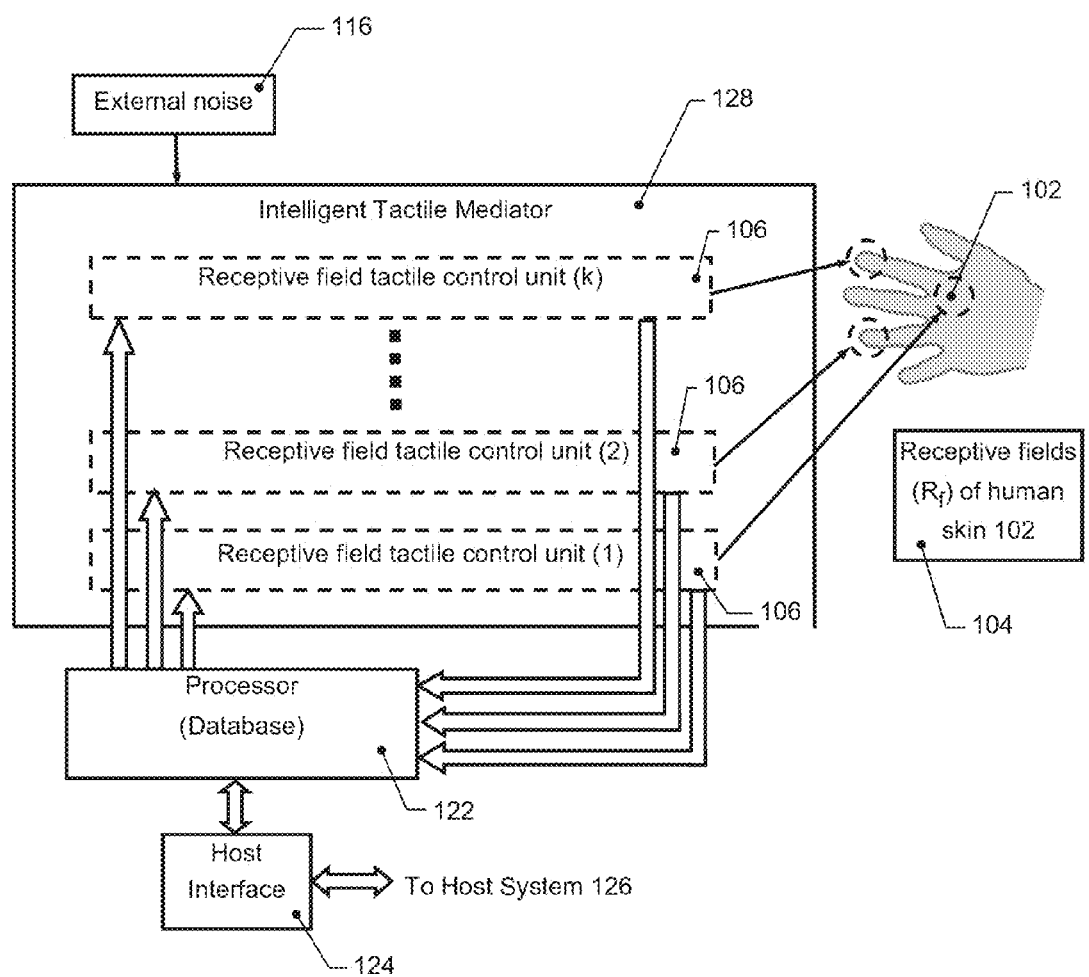
FIG. 2 illustrates a tactile imaging system according to an alternative embodiment which includes a plurality of individually controllable the Rf tactile control units.

FIG. 2 illustrates an alternative embodiment of the tactile imaging system wherein a plurality of Rf-tactile control units 106 are provided as a mesh of distributed components integrated into the body of the tactile intelligent mediator 128 to be brought into contact with receptive fields 104 of the human skin 102. Distributed components may be layered or assembled into functionally complete units connected with the processor 122 through the data/control bus using any suitable techniques for wiring and wireless data transfer and power supply/charging.

For instance, a layered MFC (macro-fiber composites) or EAP (electro-active polymers) actuators may be embedded into the body of the tactile mediator along with fiber sensors (e.g., force and pressure, strain and temperature sensors based on polymer or silica fiber Bragg gratings).

Figure 3A:
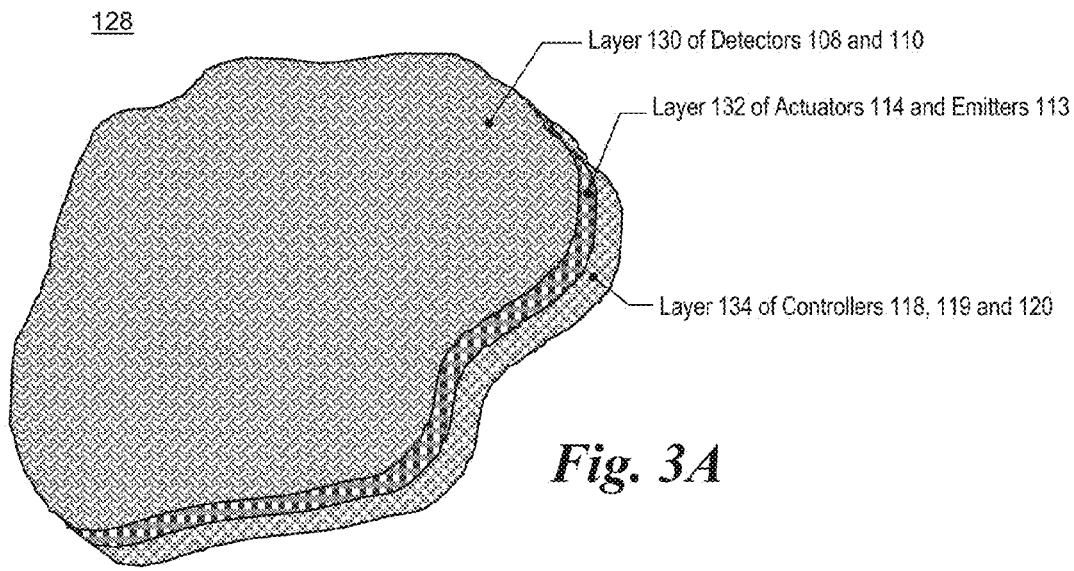
FIG. 3A illustrates a layered structure of the tactile imaging system.
Figure 3B:
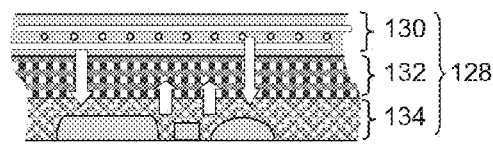
FIG. 3B is a sectional view exemplifying a triple-layered structure.
Figure 3C:
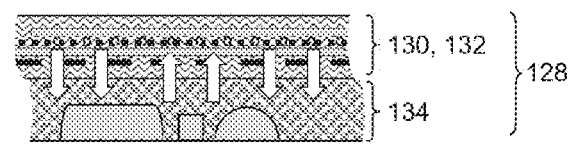
FIG. 3C is a sectional view exemplifying a double-layered structure.

FIGS. 3A, 3B and 3C exemplify the layered structure of the tactile imaging system. In particular, the tactile mediator may be composed of three layers as shown in FIG. 3B, or may be composed of two layers as shown in FIG. 3C.

As shown in FIGS. 3A and 3B, an external layer 130 presents a flexible and deformable coating material (for example, made of silicone, polyurethane sheets, fabrics or a composite gel-like substance with structure-forming excipients) having embedded matrix of fiber sensors in a kind of a rectangular X-Y grid or distributed in other way across each surface of the Rf tactile control unit. The external layer 130 contains a plurality of skin status detectors 108 and a plurality of signal propagation detectors 110, and thus has a function of detecting tactile signals' propagation through the tactile mediator 128.

As shown in FIG. 3B, an internal layer 132 contains a plurality of tactile actuators 114 and a plurality of non-contact signal emitters 113 which may be implemented with the use of any suitable technology and arranged according their specification to efficiently generate tactile signals and patterns. Besides of tactile actuators, this (internal) layer may contain other type of actuated components, fibers and excipients which may change mechanical, thermal and electrical (conductivity) characteristics of mediator that impact on the propagation of tactile signals to the human skin and conditions of touch contact. The third layer 134 presents a flexible and deformable circuit board with integrated wireless power supply system and the actuator controllers 118, the emitter controllers 119 and the mediator controllers 120.

The external layer 130 and the internal layer 132 may be coupled into a single layer as indicated on FIG. 3C. In this case, for example, the tactile actuator 114 may be provided as a self-sensing transducer which is capable of functioning not only as a sensor but also as an actuator, and the skin status detector 108 and the signal propagation detector 110 may be omitted.

Figure 4:
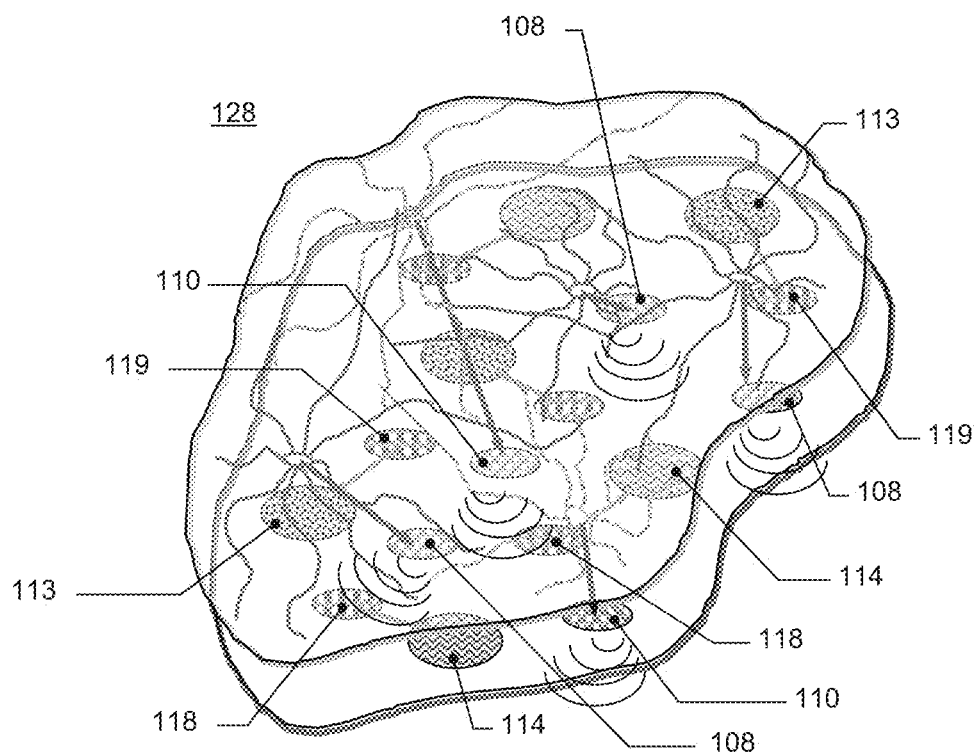
FIG. 4 illustrates a double-layered neuron-like structure (nodes) of sensors located in an external layer and actuators located in the second (internal) layer together with controllers.
Figure 4:
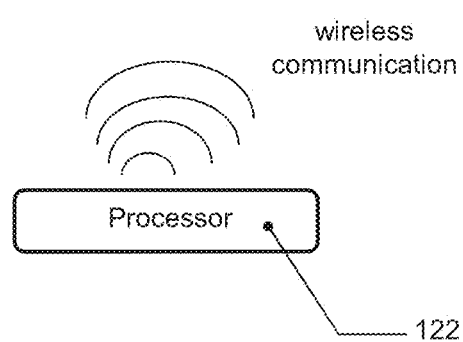

As shown in FIG. 4, the tactile imaging system may be configured as a highly integrated miniature neuron-like structures of sensors coupled with actuated fibers that present modular functional nodes information flow from which may be collected by the detectors 108 and 110 and send to the processor 122 of tactile imaging system, for example, through the wireless communication.

Afferent information from sensors of the same Rf-control unit and of the same modality (mechanical, thermal, electrical) or/and test signals may be collected from groups of neurons-like sensors by the modality-specific nodes located in the second layer 134 of the tactile imaging system and being pre-processed before sending to the processor 122.

While method have been described in terms of several embodiments, those skilled in the art will recognize that the design and methods are not limited to the embodiments described, but may be practiced with modification and alteration within the spirit and scope of the appended claims. The description is thus to be regarded as illustrative instead of limiting.

The invention claimed is:

1. A tactile imaging system comprising:
a receptive field tactile control unit; and
a connecting module configured to connect the tactile imaging system with a host system,
wherein the receptive field tactile control unit includes:
  a monitoring module configured to monitor a property of a human skin; and
  a tactile stimulation providing module configured to provide a tactile stimulation,
wherein the connecting module includes:
  a processor; and
  a host interface,
wherein the processor generates a contact event based on information received from the monitoring module, and
wherein the processor controls the tactile stimulation based on an effect parameter stored in a memory thereof or based on information received from the host system through the host interface.

2. The tactile imaging system of claim 1,
wherein the receptive field tactile control unit further includes
  a tactile mediator configured to change a skin contact status with respect to the human skin.

3. The tactile imaging system of claim 2,
wherein the monitoring module monitors a propagation of the tactile stimulation through the tactile mediator to the human skin.

4. The tactile imaging system of claim 2,
wherein the tactile mediator includes:
  a substance or/and an embedded component which are able to change the skin contact status with respect to the human skin in response to an applied agent such as an electrical current, a magnetic field and an LED light having a specific spectrum.

5. The tactile imaging system of claim 1,
wherein the tactile stimulation providing module includes:
  an actuator configured to generate the tactile stimulation; and
  a controller configured to adjust a parameter of the tactile stimulation.

6. The tactile imaging system of claim 1,
wherein the receptive field tactile control unit includes a controller configured to control a parameter of the tactile mediator.

7. The tactile imaging system of claim 1,
wherein the monitoring module monitors an external noise in the absence of the contact with the human skin and in the absence of the tactile stimulation generated by the actuator.

8. The tactile imaging system of claim 1,
wherein the processor controls the parameter of the tactile stimulation based on information received from the monitoring module so as to compensate an attenuation and a distortion caused by an external noise.

9. The tactile imaging system of claim 1,
wherein the monitoring module includes
  an embedded sensor configured to control at least one of a temperature, a humidity, a conductivity, and a blood vessel pulsing as the skin contact status when the tactile imaging system is in contact with or closely faces with the human skin.

10. The tactile imaging system of claim 1,
wherein the processor controls the parameter of the tactile stimulation based on information received from the monitoring module so as to compensate a change of a skin sensitivity of the human skin being in contact with tactile mediator.

11. The tactile imaging system of claim 1,
wherein the receptive field tactile control unit is provided in plurality and is integrated into a tactile intelligent mediator.

12. The tactile imaging system of claim 11,
wherein the tactile intelligent mediator has a multi-layered structure in which sensors, actuators, wireless power sources and data transfer lines are distributed.

13. The tactile imaging system of claim 12,
wherein the tactile intelligent mediator is formed to be deformable and includes:
an external layer in which the monitoring module is embedded in plurality;
an internal layer in which the tactile stimulation providing module is embedded in plurality; and
another layer in which the controller is embedded in plurality.

14. The tactile imaging system of claim 12,
wherein the tactile intelligent mediator is formed to be deformable and includes:
a first layer in which the monitoring module and the tactile stimulation providing module are embedded in plurality; and
a second layer in which the controller is embedded in plurality.

15. The tactile imaging system of claim 14,
wherein the tactile stimulation providing modules in the first layer are implemented as layered macro-fiber composites or/and electro-active polymers.

16. The tactile imaging system of claim 12,
wherein the monitoring module is implemented as distributed smart sensors having a mesh-like or a neuron-like fiber-based structure.

17. The tactile imaging system of claim 12,
wherein the tactile intelligent mediator is configured to change the skin contact status at a contact area, and a thermal condition and a humidity in a position neighboring to the contact area.

18. A tactile imaging system comprising:
a receptive field tactile control unit; and
a connecting module configured to connect the tactile imaging system with a host system,
wherein the receptive field tactile control unit includes:
a monitoring module configured to monitor a property of a human skin; and
a tactile stimulation providing module configured to provide a tactile stimulation
wherein the receptive field tactile control unit is provided in plurality and is integrated into a tactile intelligent mediator,
wherein the tactile intelligent mediator has a multi-layered structure in which sensors, actuators, wireless power sources and data transfer lines are distributed,
wherein the monitoring module is implemented as distributed smart sensors having a mesh-like or a neuron-like fiber-based structure, and
wherein information received from sensors of different modality are collected or/and preprocessed by modality-specific nodes having wireless connection with the processor.

* * * * *